US006803185B1

(12) United States Patent
Graham et al.

(10) Patent No.: US 6,803,185 B1
(45) Date of Patent: *Oct. 12, 2004

(54) METHOD TO MEASURE ACYL-COENZYME A ESTERS

(75) Inventors: Ian Alexander Graham, York (GB); Tony Robert Larson, Leeds (GB)

(73) Assignee: The University of York, York (GB)

( * ) Notice: Subject to any disclaimer, the term of this patent is extended or adjusted under 35 U.S.C. 154(b) by 423 days.

(21) Appl. No.: 09/980,167

(22) PCT Filed: May 30, 2000

(86) PCT No.: PCT/GB00/02061
§ 371 (c)(1),
(2), (4) Date: Feb. 19, 2002

(87) PCT Pub. No.: WO01/09610
PCT Pub. Date: Feb. 8, 2001

(30) Foreign Application Priority Data

May 28, 1999 (GB) .............................. 9912382

(51) Int. Cl.[7] .............................. C12Q 1/00; C12Q 1/44; C12Q 1/32
(52) U.S. Cl. ................................ 435/4; 435/19; 435/26; 435/968; 435/975
(58) Field of Search .............................. 435/4, 19, 968, 435/975

(56) References Cited

FOREIGN PATENT DOCUMENTS

| EP | 1181556 A1 | * | 2/2002 |
| WO | WO 200109610 A1 | * | 2/2001 |

OTHER PUBLICATIONS

Peterson et al;Biochemistry and Molecular Bio;V.39(41);pp. 12659–70;(1Oct. 17, 2000).*
Easton et al., "The Effect of Respiratory Chain Impairment on β–Oxidation in Rat Heart Mitochondria," *Biochem. J.*, 319: 633–640 (1996).
Eaton et al., "Mammalian Mitochondrial β–Oxidation," *Biochem. J.*, 320: 345–357 (1996).
C. Tamvakopoulos & V. Anderson, "Detection of Acyl–Coenzyme A Thioester Intermediates of Fatty Acid β–Oxidation as the N–Acylglycines by Negative–Ion Chemical Ionization Gas Chromatography–Mass Spectrometry," *Analytical Biochemistry*, 200: 381–387 (1992).
Demoz et al., "Separation and Detection of Tissue CoASH and Long–Chain Acyl–CoA by Reversed Chromatography After Precolumn Derivatization with Monobromobimane," *Journal of Chromatography*, 635: 251–256 (1993).

* cited by examiner

*Primary Examiner*—Louise N. Leary
(74) *Attorney, Agent, or Firm*—Myers Bigel Sibley & Sajovec, PA

(57) ABSTRACT

The invention provides a method for measuring an acyl coenzyme A (acyl CoA) ester or esters in a sample, comprising the steps of: a) forming a reaction mixture comprising the sample to be tested and a derivatizing agent; b) allowing the sample and said derivatizing agent to react, so as to form a fluorescent derivative(s) of any acyl CoA ester(s) present in the sample; and c) determining a level of said fluorescent derivative(s). Further provided is an assay for determining the level of an acyl coenzyme A (acyl CoA) ester or esters in a test sample, comprising the steps: a) obtaining the test sample from an organism to be tested; b) forming a reaction mixture comprising the sample to be tested and a derivatizing agent; c) allowing the sample and said derivatizing agent to react, so as to form a fluorescent derivative(s) of any acyl CoA ester(s) present in the sample; d) determining a level of said fluorescent derivative(s) ester(s); and e) comparing the level of said fluorescent derivative(s) in the test sample with a level of said fluorescent derivative(s) in a normal sample, such that a significant difference in the level of said fluorescent derivative(s) between the test sample and normal sample may be predictive of a fatty acid oxidation disorder in said organism. Also disclosed is a kit for use with the assay of the present invention.

26 Claims, 6 Drawing Sheets

METHOD TO MEASURE ACYL-COENZYME A ESTERS

Figure 1:
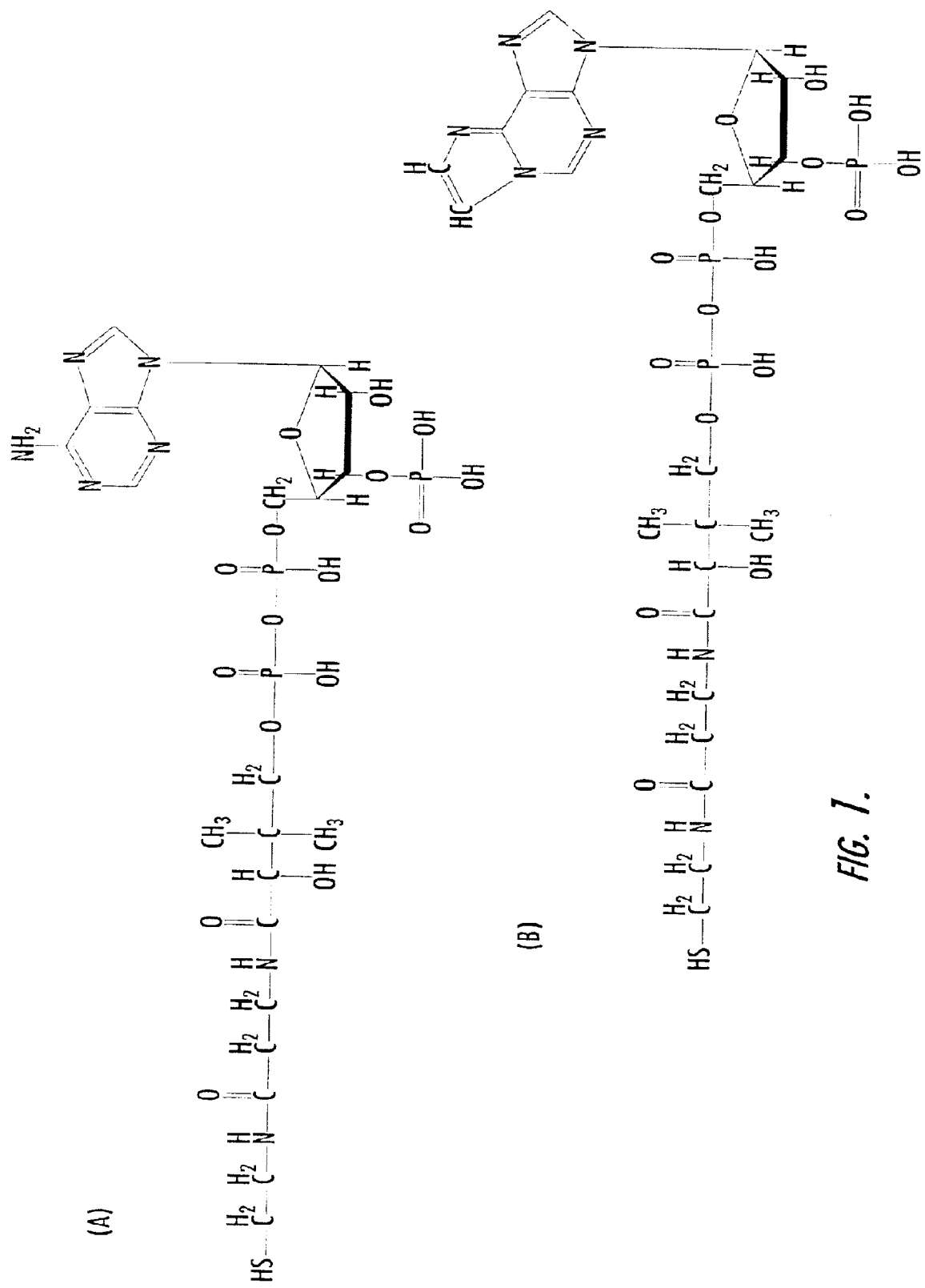

The present application is a U.S. national phase application of PCT International Application No. PCT/GB00/02061, having an international filing date of May 30, 2000 and claiming priority from British Patent Application No. GB9912382.0, filed May 28, 1999, the disclosures of which are incorporated herein by reference in their entirety. The above PCT International Application was published in the English language and has International publication No. WO 01/09610 A1.

The present invention relates to a method and assay for determining a level of an acyl coenzyme A ester or esters in a sample. The method and/or assay finds particular application in screening and prediction of human fatty acid oxidation disorders.

Measurement of acyl coenzyme A (CoA) esters may have important utility in the diagnosis of human fatty acid oxidation (FAO) disorders. Up to 5%; of sudden infant death occurrences are likely to be a consequence these disorders (Boles et al. 1998).

The most common FAO disorder in medium chain acyl CoA dehydrogenase (MCAD) deficiency, which may affect up to 1 in 6400 new-borns in the UK (Eaton et al. 1996). MCAD deficiency is easily treated by avoiding fasting; however there is no currently accepted screening protocol for this disease. Universal screening for MCAD in the UK has been recommended (Bonnet et al. 1998, Clayton et al. 1998, Pollit and Leonard 1998). Other conditions where fatty acid metabolites may be problematic include the remission of protein energy malnutrition (PEM) in infants, where toxic acyl CoA compounds may accumulate and contribute to worsening of patient condition (Terangarcia et al. 1998).

FAO disorders result in a variety of abnormal urinary and blood plasma metabolite levels; however screening is conventionally carried out on tissue biopsies (Eaton et al. 1996). This makes wide-scale neonatal screening by this method impractical. MCAD deficiency and other FAO disorders are currently diagnosed by the generation and measurement of radiolabeled acyl CoA products with atypical chain lengths from radiolabeled precursor. An alternative diagnostic procedure is to use the polymerase chain reaction (PCR) technique to identify the relevant gene(s), but this is only 85 to 90% accurate (Eaton et al. 1996). Diagnosis of MCAD deficiency and other FAO disorders would benefit most from the application of simple methods to routinely and directly measure changes in the concentrations of plasma and urine metabolites, such as acyl CoA esters.

Routine monitoring of acyl CoA ester concentrations in tissues has not been attempted because of the absence of suitable low cost, high throughput screening methodologies. Traditional detection methods for these compounds utilize high performance liquid chromatography (HPLC) coupled with ultraviolet (UV) absorption. This method can detect down to approximately 500–1000 fmoles of acyl CoA esters. This method is not however sensitive enough to reliably detect changes in ratios of acyl CoA esters associated with FAO disorders. A newer technique, which involves glycine aminolysis, pentafluorobenzyl bromide esterification, and gas chromatography/mass spectrometry can detect acyl CoA esters at concentrations as low as 30 fmoles (Tamvakopoulous and Anderson 1992). However, this method is time-consuming, complex, and requires expensive kit.

It is amongst the objects of the present invention to obviate and/or mitigate at least one of the aforementioned disadvantages.

In a first aspect the present invention provides a method for measuring an acyl coenzyme A (acyl CoA) ester or esters in a sample, comprising the steps of:
a) forming a reaction mixture comprising the sample to be tested and a derivatizing agent;
b) allowing the sample and said derivatizing agent to react, so as to form a fluorescent derivative(s) of any acyl CoA ester(s) present in the sample; and
c) determining a level of said fluorescent derivative(s).

It is to be understood that the acyl CoA esters of the present invention are of the form where a fatty acid is linked to coenzyme A by way of a thioester linkage between the carboxyl group of the fatty acid and the sulfhydryl group of CoA. Fatty acids are in fact typically oxidised by first forming such an acyl CoA ester as described and thereafter sequential rounds of degradation by acyl CoA dehydrogenases which have different acyl chain-length specificity.

The method may be used for example to measure levels of acyl CoA esters present in plant tissue where it could have application in improving yield of unusual fatty acids in oil seed crops engineered to produce the same. However, the method finds particular application in measuring levels of acyl CoA esters in samples obtained from an animal and subsequent determination of any possible fatty acid oxidation (FAO) disorders in the animal.

Thus, in a second aspect the present invention provides an assay for determining a level of an acyl coenzyme A (acyl CoA) ester or esters in a test sample, comprising the steps of:
a) obtaining the test sample from an organism to be tested;
b) forming a reaction mixture comprising the sample to be tested and a derivatizing agent;
c) allowing the sample and said derivatizing agent to react, so as to form a fluorescent derivative(s) of any acyl CoA ester(s) present in the sample;
d) determining a level of said fluorescent derivative(s) ester(s); and
e) comparing the level of said fluorescent derivative(s) in the test sample with a level of said fluorescent derivative(s) in a normal sample, such that a significant difference in the level of said fluorescent derivative(s) between the test sample and normal sample may be predictive of a fatty acid oxidation disorder in said organism.

The organism to be tested may be any suitable organism which metabolises acyl CoA esters. However the assay is particularly suited to testing animals, such as cows, sheep, dogs, cats, goats, pigs, horses and especially humans. It is envisaged that the assay may be used to test newborns in order to determine if the newborn has any fatty acid oxidation disorder, such as MCAD deficiency, or any other disorder which results in alteration of acyl CoA levels, such as protein energy malnutrition. Fatty acid oxidation disorders may be associated with an accumulation or depletion of certain acyl CoA esters in comparison to normal levels.

The test sample may be any sample in which acyl CoA esters are present. For example the test sample may be a sample of tissue taken from the organism. However, it is preferred that the sample to be tested is obtained from the organism with the minimum of distress or discomfort to the organism. Thus, for animals the preferred source of the sample is from the blood, eg. plasma, or urine. A urine sample is particularly preferred since obtaining the sample is non-invasive. other samples may include samples from tears, nasal or vaginal swabs.

The derivatizing agent may be any agent which upon reaction with an acyl CoA renders the acyl CoA sufficiently fluorescent such that the fluorescent acyl CoA derivative may be detected at low concentrations. Typically the fluorescent acyl CoA derivative may be detected at concentrations less than 100 pmoles, for example less than 50 pmoles, such as less than 5 pmoles. The presently described method may even be used to detect acyl CoA esters in the 10s of fmol range. The skilled reader will appreciate that the sensitivity of the present method will depend to some extent on the derivatizing agent employed and the degree to which the acyl CoA is rendered fluorescent.

It may be possible to form fluorescent derivatives of acyl CoA esters with a number of amino reactive probes, amino derivatization reagents or protein labelling reagents. These reagents may act to modify the amine group on the coenzyme A adenine ring to form fluorescent derivatives. These may include, but are not limited to the commonly used reagents chloroacetaldehyde, dansyl or dabsyl chloride, napthalens-2,3-dicarboxyaldehyde (NDA), fluorescein, and o-phthaldialdehyde (OPA).

Generally speaking the derivatizing agent may react with the amine group on the coenzyme A adenine ring to form the fluorescent derivative(s). For example, the present inventors have found that the use of chloracetaldehyde as the derivatizing agent results in the amine being derivatized with the formation of an etheno group.

The fluorescent derivatives of the acyl CoA esters may be conveniently detected using a fluorometer. Typically there will be a number of acyl derivatives in any particular sample and in order to accurately determine their presence it is also necessary to separate them in some manner. Thus, separation may be preformed using HPLC techniques commonly known in the art with the fluorometer coupled to the HPLC to detect the fluorescence of the acyl CoA derivatives.

It is immediately evident to one skilled in the art that in order to determine if the level of an acyl CoA in a test sample is abnormal or deficient it is necessary to compare the level determined in the test sample with a control and/or normal sample. Thus, in accordance with the assay a control sample, comprising known amounts of particular acyl CoA esters having varying length acyl groups (eg. $C_2$–$C_{16}$) may be run in conjunction with the test sample in order to allow identification and quantification of the acyl CoA esters in the test sample. Additionally, or optionally, a normal sample may also be run with the test sample. A normal sample would be a sample from a healthy organism which does not have a fatty acid oxidation disorder. This would allow comparison of the normal and test sample results and determination of whether or not any level of acyl CoA in the test sample is significantly different to a normal sample.

It is expected that, for example, a subject displaying an MCAD deficiency may have nigher levels of medium chain acyl CoA esters (eq. $C_8$–$C_{12}$) in comparison to a normal sample.

In a further aspect there is provided a kit for use with the assay of the present invention, the kit comprising a derivatizing agent for fluorescently derivatizing an acyl CoA ester(s) present in a test sample; and a normal and/or control sample for comparing the level of said acyl CoA esters(s) in the test sample with the level of acyl CoA ester(s) in the normal and/or control sample.

The normal and/or control sample(s) may already be derivatized or may be derivatized in conjunction with the test sample by the derivatizing agent.

The present invention will now be further described by way of example and with reference to the accompanying figures wherein:

FIG. 1 shows the structure of the CoA portion of an acyl CoA ester prior to derivatization, (A); and after derivatization with chloroacetaldehyde (B).

Figure 2:
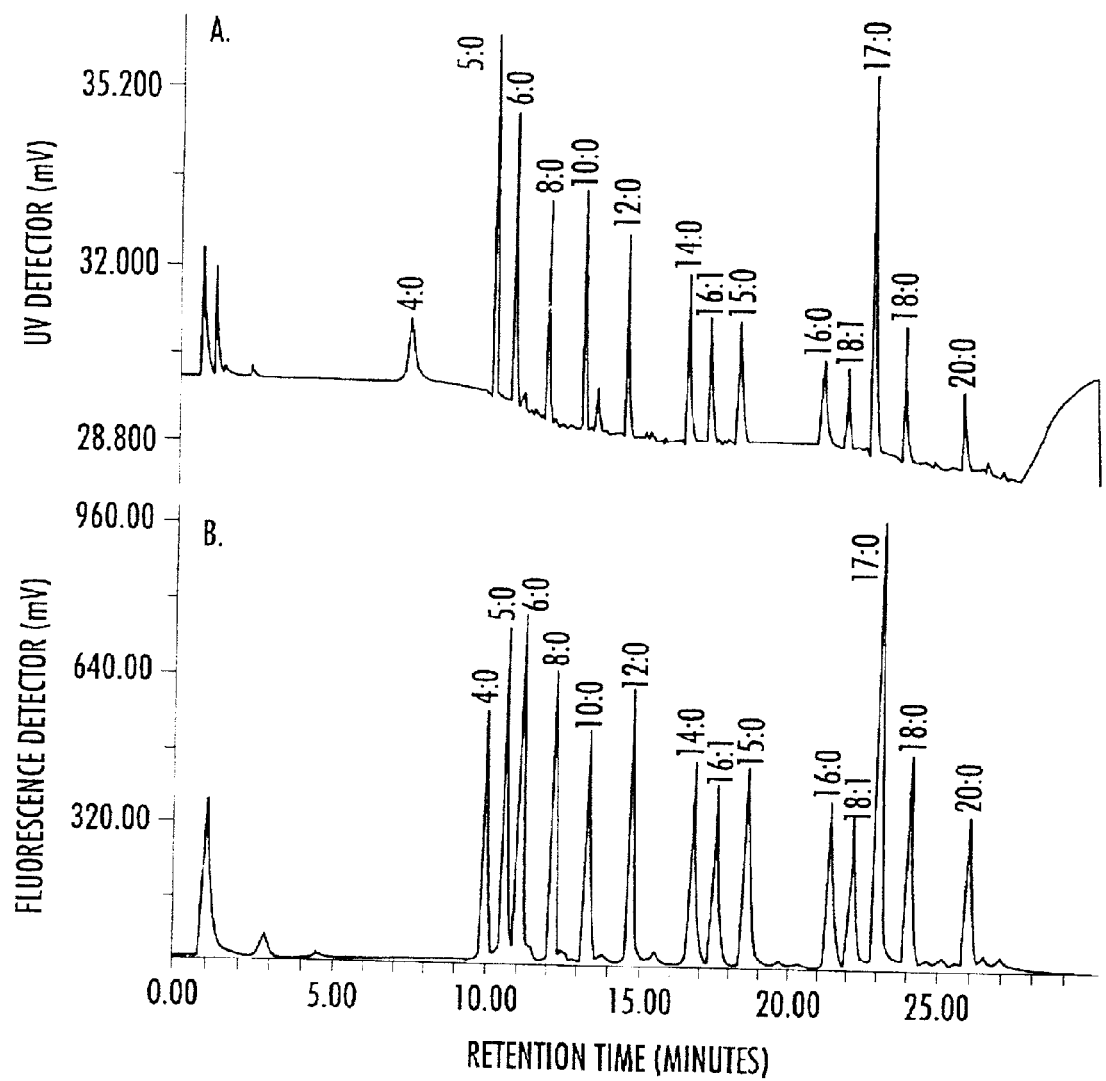
Figure 3:
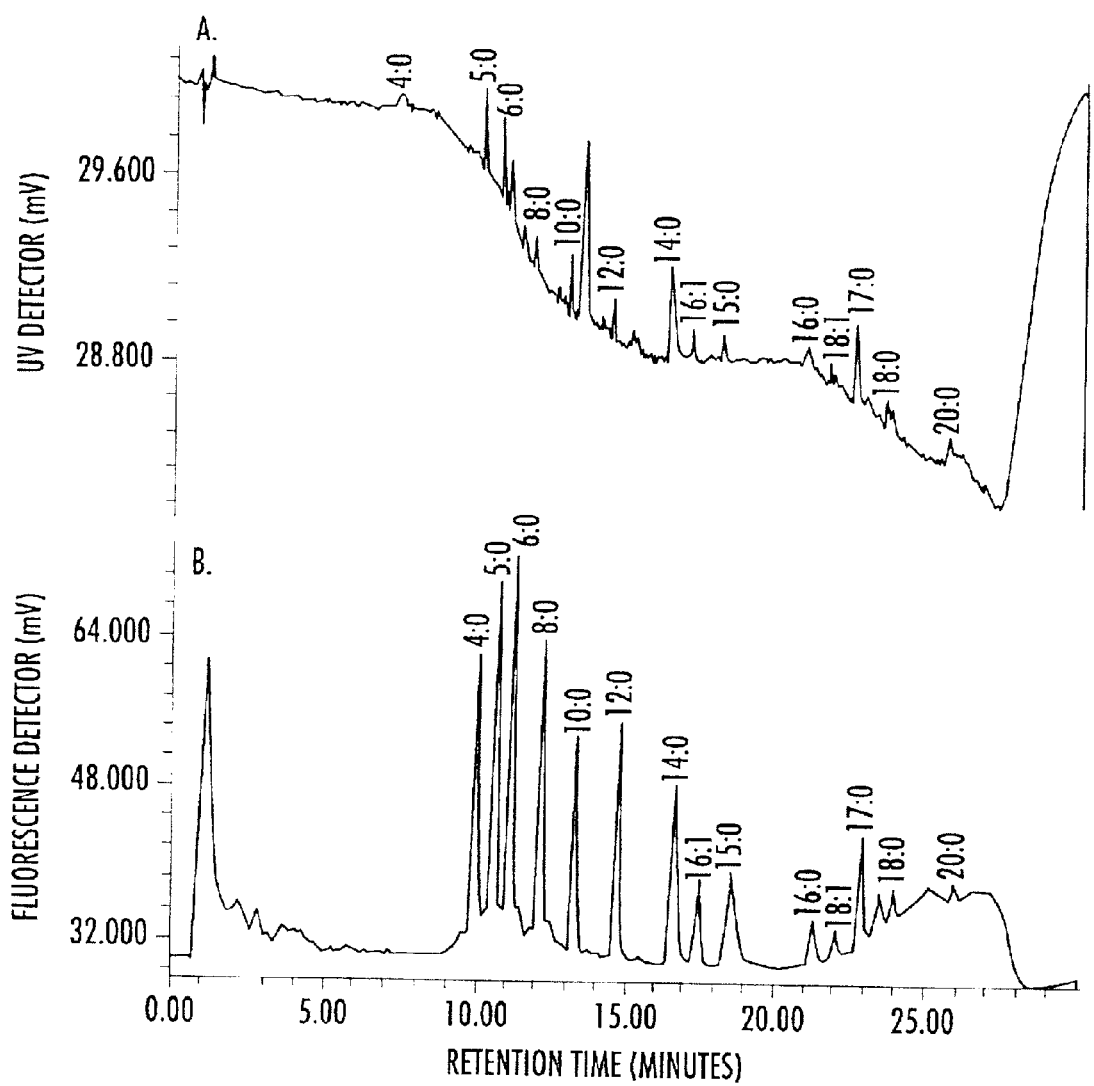
Figure 4:
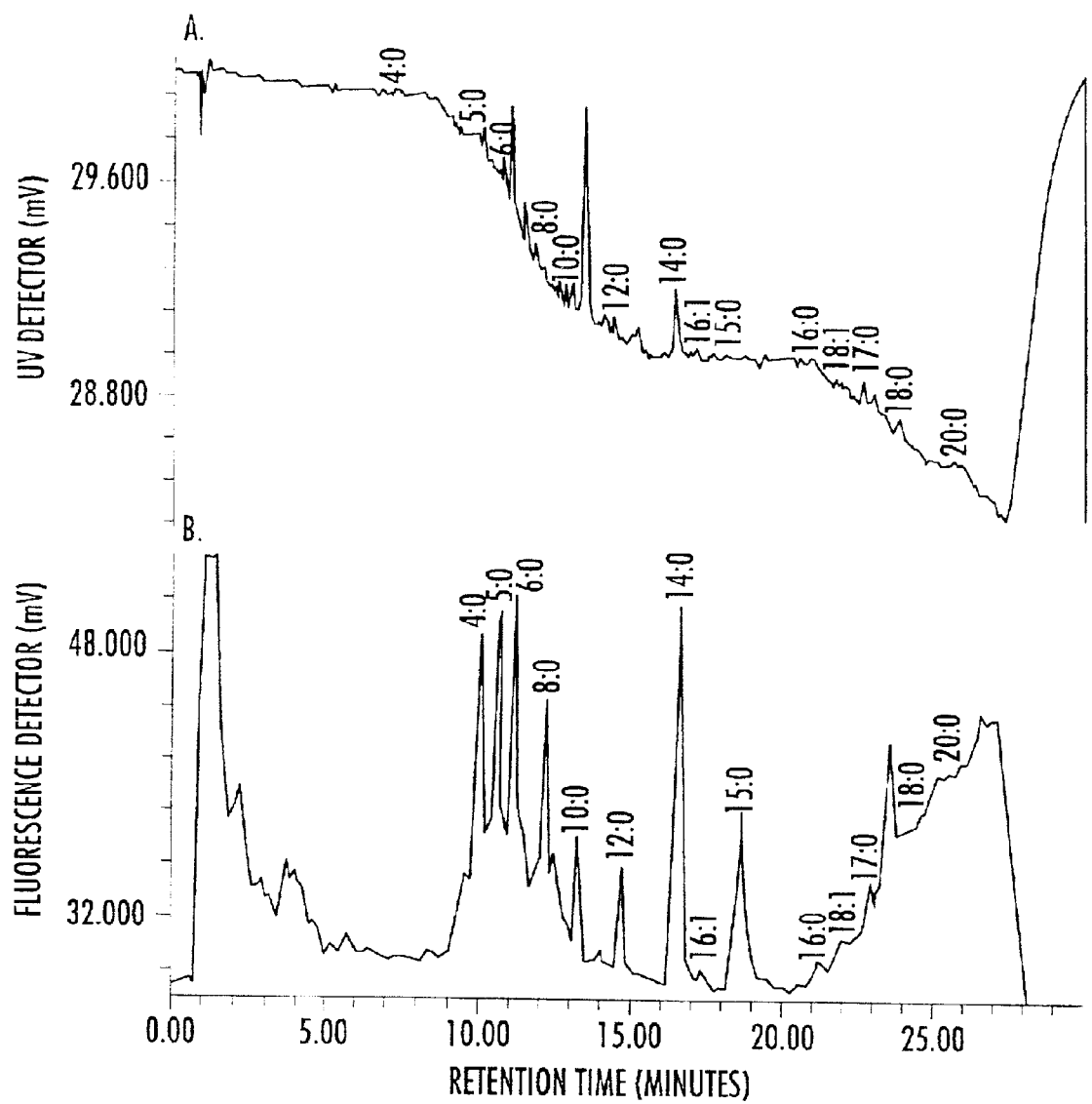

FIGS. 2–4 show HPLC chromatograms of a detector response using a previously described UV based method (A) in comparison to the presently disclosed fluorescent based method (B) for measuring a range of acyl CoAs; Specifically, FIG. 2 shows chromatograms of 500 pmol individual acyl CoA esters. UV(A) or fluorescence (B) chromatograms were obtained from equivalent concentrations of non-derived or derived standard acyl CoA esters, respectively. The identity of individual acyl CoA esters, based on the number of carbons and double bonds in the acyl chain, is shown above each peak; and FIG. 3 shows chromatograms of 50 pmol individual acyl CoA esters; and FIG. 4 shows chromatograms of 2.5 pmol individual acyl CoA esters.

Figure 5:
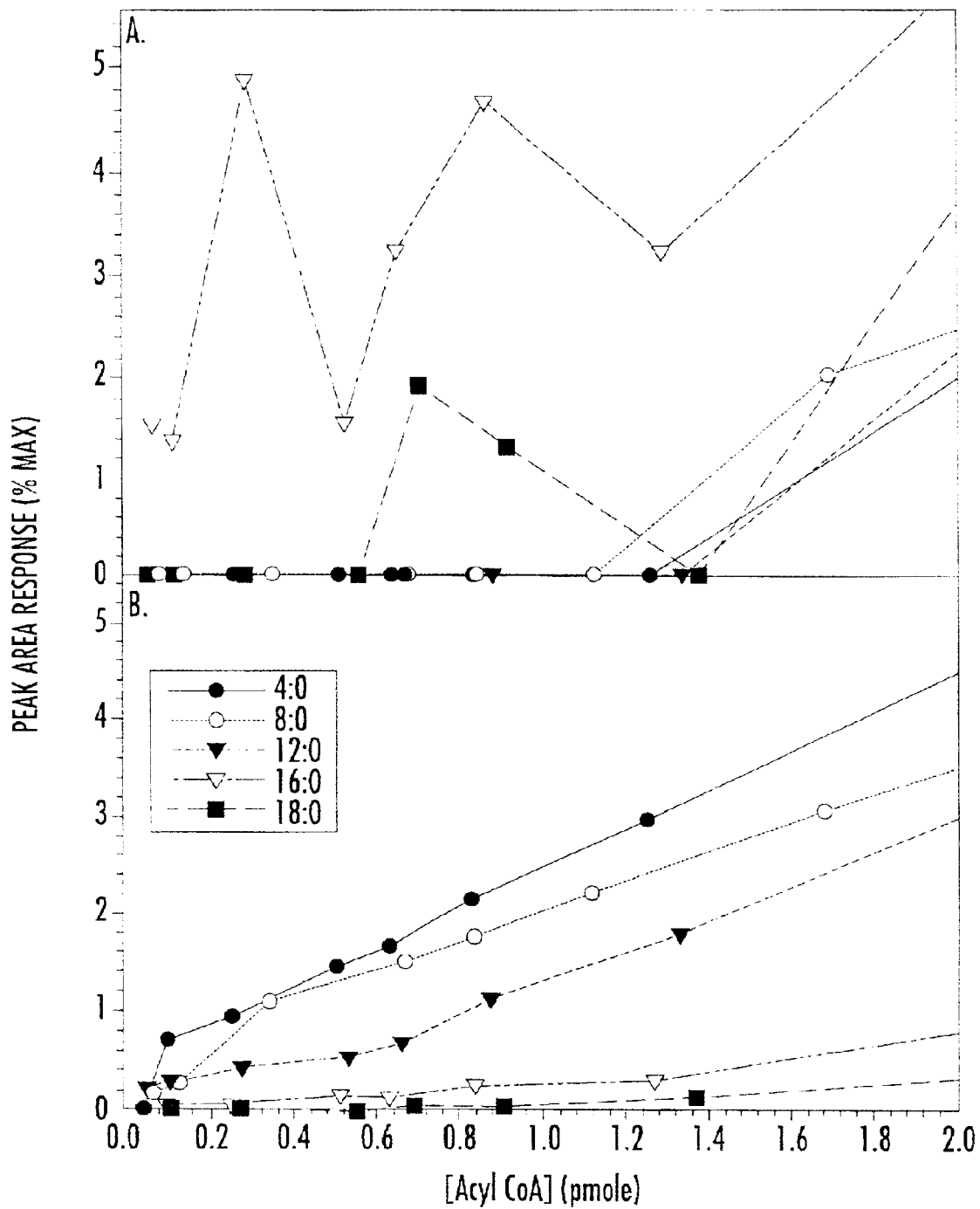
Figure 6:
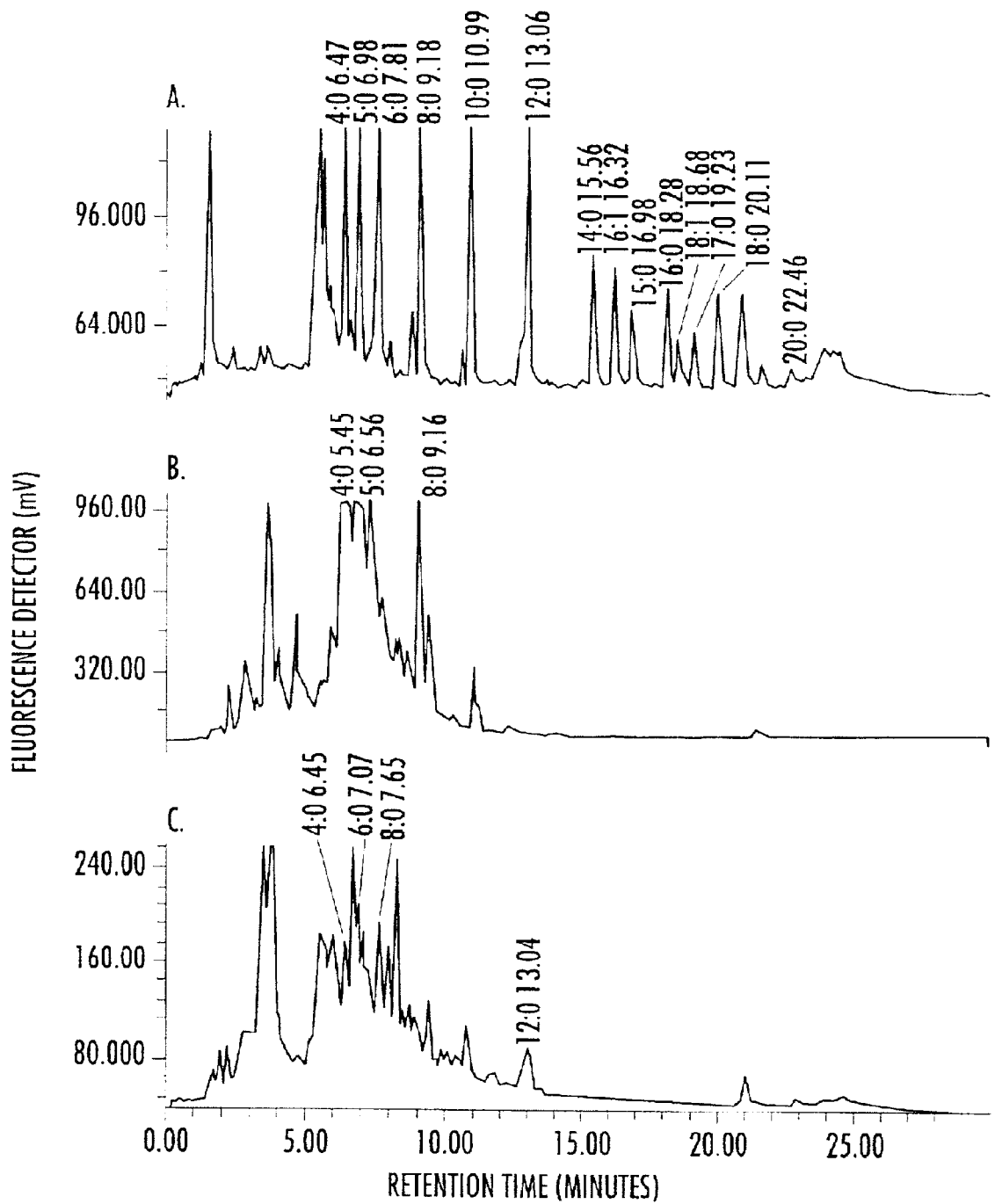

FIG. 5 shows a comparison of the linearity of detector response between the previously described UV and presently disclosed fluorescent methods for low concentrations of selected acyl CoAs. More specifically, FIG. 5 shows calibration curves for the quantitation of selected individual acyl CoA esters. UV or fluorescence chromatograms were generated from a dilution series of non-derived or derived standard acyl CoA esters, respectively. The calculated concentrations of the fatty acyl CoA esters (A) and their fluorescent derivatives (B) are shown plotted against the percentage of the maximum peak areas of ca.50–70 pmol of the individual compounds; and FIG. 6 shows chromatograms which display the retention times of fluorescent derivatives of acyl CoA standards, (A), acyl CoAs in human urine, (B); and acyl CoAs in human plasma, (c).

EXAMPLES SECTION

Methods

Purified acyl CoA esters were obtained from Sigma Chemical Company (Dorset, UK) as their lithium salts. These were used to formulate standard solutions ranging in concentration from 1.5 to 10 mM. The acyl CoA esters used (in each case, the formula for the acyl CoA ester is based on the carbon number (x) and number of double bonds (y) of the acyl chain, and is represented by x:y) included: n-butyryl (4:0), n-valeryl (5:0), n-hexanoyl (6:), n-octanoyl (8:0), n-decanoyl (10:0), lauroyl (12:0), myristoyl (14:0), n-pentadecanoyl (15:0), palmitoyl (16:0), palmitoleoyl (cis) (16:1), n-heptadcanoyl) (17:0), stearoyl (18:0), oleoyl (cis) (18:1), and arichidoyl (20:0).

Human blood plasma was prepared from fresh anticoagulated whole blood by centrifugation at 3000×g for 10 minutes. The plasma was aliquoted and stored at −80° C. Acyl CoA ester extracts were made from 100 $\mu$L of thawed human blood plasma. This was combined with 100 $\mu$L 50 mM $KH_2PO_4$ buffer, pH 7.2 (which also contained 10 mM $MgCl_2$ and 2 $mgmL^{-1}$ fatty acid free bovine serum albumin), 100 $\mu$L isopropanol, and 2.5 $\mu$L glacial acetic acid. The samples were vortex-mixed and washed three times with 200 $\mu$L petroleum ether saturated with 1:1 (v/v) isorpopanol:water to remove free fatty acids present in the sample. To each sample was added 5 $\mu$L saturated ammonium sulphate and 600 $\mu$L 2:1 (v/v) methanol:chloroform. The samples were left to flocculate on the bench for 20 minutes before centrifuging at 21 000×g for 2 minutes. The supernatant containing the acyl CoA esters was transferred to a fresh tube and evaporated to dryness in a SpeedVac Plus (Savant Instruments) over 90 minutes.

Fresh urine samples were extracted in chloroform:methanol. To 3 mL of 2:1 chloroform:methanol (v/v) was added 0.8 mL urine. This was vortex-mixed and centrifuged at low speed for 5 minutes to separate the phases. The lower organic phase was evaporated to dryness as described above.

Fluorescent acyl CoA ester derivatives were made by reacting solutions containing acyl CoA esters with buffered derivitizing reagent. Equal volumes of this reagent was mixed with either standard acyl CoA ester solutions or the lyophylized samples reconstituted in distilled water. The derivitizing reagent contained 1 M chloroacetaldehyde solution in 300 mM sodium acetate buffer, pH 4.0. Chloroacetaldehyde was obtained as a 50% (v/v) solution in water from Aldrich (Dorset, UK). The samples were then heated to 100° C. for 10 minutes to complete the derivitization process. The derivitized samples were then clarified by centrifugation at 21000×g for 2 minutes and the supernatant transferred to HPLC vials.

Chromatograms were generated using a gradient elution system, with 10 mM $KH_2PO_4$, pH 7.0 as solvent A and 10 mM $KH_2PO_4$ dissolved in 70% acetonitrile, pH 7.0 as solvent B. Alternatively, 50 mM $KH_2PO_4$, pH 7.0 was used as solvent A and unbuffered 70% acetonitrile as solvent B. The gradient elution program was as follows: 0.02 to 12 minutes increasing from 0% to 55% B with a negative exponential slope of −2 (Shimadzu, Kyoto program on SCL-10Avp system controller); 12 to 20 minutes increasing from 55% to 100% B with a positive exponential slope B of 1; 20 to 23 minutes isocratic 100% B; 23 to 25 minutes linear gradient from 100% to 0% B; 25 to 30 minutes isocratic 0% B. The mobile phase flow-rate was kept at 1 $mL.min^{-1}$. Injection volumes ranged from 5 to 50 μL. Peaks were resolved by either a platinum rocket C18 3μm 53 mm×7 mm reversed phase column (Alltech, Carnforth, Lancashire, UK), or a TSKgel super ODS 2μm 50 mm×4.6 mm reversed phase column (Tosoh corporation, Japan). The columns were kept at 40° C. during runs. Non-derived acyl CoA esters were monitored by UV absorbance at 260 nm. The derived acyl CoA esters were monitored by fluorescence with the excitation wavelength set at 305 nm and the emission wavelength set at 420 nm.

EXAMPLE 1
Determination of Site of Derivatization of any Acyl CoA Ester Reacted with Chloroacetaldehyde The chemical structures of non-derived and chloroacetaldehyde-derived decanoyl CoA esters were compared using mass spectrometry/mass spectrometry (MS/MS). Individual acyl CoA esters and their derivatives were separated by injecting 50 μL aliquots of standard mixtures through a Hypersil C18 column using a mobile phase containing 20 mM ammonium acetate and 90% acetonitrile. The acyl CoA esters and their derivatives were monitored by their UV absorbance at 260 nm. The effluent from the column was introduced at 1 mL/min into a Thermoquest LC Duo mass spectrometer fitted with an electrospray ionisation (ESI) source. The mass spectrometer was operated in positive ionisation mode with collision energy set to 25%. Secondary fragments were produced by targeted MS/MS on the parent ions associated with individual acyl CoA esters and their derivatives.

Chromatograms of underivatized and derivatized decanoyl CoA esters were obtained (data not shown).

The results were consistent with the addition of 24 mass units to the adenine moiety of the coenzyme A molecule, forming a coenzyme A etheno derivative (see FIG. 1(B)).

EXAMPLE 2
Comparison of Current UV Based Method with New Fluorescent Method

Samples of various acyl CoA esters were prepared as described in the method section and chromatograms of a mixture of acyl CoAs generated as described.

It can be seen from FIG. 2 using either a UV based method or the presently described florescent based method that at a concentration of 500 pmol the individual acyl CoA esters are readily resolved and detected (the identity of individual acyl CoA esters, based on the number of carbons and double bonds in the acyl chain, is shown above each peak). However at a concentration of 50 pmol (FIG. 3) and 2.5 pmols (FIG. 4) the UV based method only poorly identifies the acyl CoA esters. The fluorescent acyl CoA derivatives however are generally speaking easily detected at 50 pmol (FIG. 2), with the lower and medium length acyl CoA esters still being easily detected and resolved at 2.5 pmol (FIG. 4).

FIG. 5 shows 4 comparison of the linearity of detector response at very low (0–2 pmol) concentrations of acyl CoA esters using the old (UV) and present (fluorescent) method. It can be seen that the linearity of response using the present method is extremely good even at such low concentrations. The old method however displays extremely poor linearity.

EXAMPLE 3
Testing of Blood and Urine Samples

Samples of blood and urine were obtained and derivatized as described in the methods section. The blood and urine samples containing the derivatised acyl CoA esters where then subjected to HPLC as described and the fluorescent acyl CoA esters detected.

FIG. 6 shows an example of a result obtained by testing a sample of urine (B) and blood plasma (C). A control sample was run in conjunction (A) and it can be seen that both the urine and blood plasma samples are identified as having a number of low and medium length fatty acyl CoA esters.

What is claimed is:

1. A method for measuring an acyl coenzyme A (acyl CoA) ester or esters in a sample, comprising the steps of:
    a) forming a reaction mixture comprising the sample to be tested and a derivatizing agent;
    b) allowing the sample and said derivatizing agent to react, so as to form a substantially intact fluorescent derivative(s) of any acyl CoA ester(s) present in the sample; and
    c) determining a level of said fluorescent derivative(s).

2. A method according to claim 1 wherein the sample to be tested is obtained from an animal.

3. A method according to claim 2 wherein the animal is a human.

4. An assay for determining a level of a acyl coenzyme A (acyl CoA) ester or esters in a test sample, comprising the steps of:
    a) obtaining the test sample for an organism to be tested;
    b) forming a reaction mixture comprising the sample to be tested and a derivatizing agent;
    c) allowing the sample and said derivatizing agent to react, so as to form a substantially intact fluorescent derivative(s) of any acyl CoA ester(s) present in the sample;
    d) determining a level of said fluorescent derivative(s) ester(s); and
    e) comparing the level of said fluorescent derivative(s) in the test sample with a level of said fluorescent derivative(s) in a normal sample, such that a significant difference in the level of said fluorescent derivative(s) between the test sample and normal sample may be predictive of a fatty acid oxidation disorder in said organism.

5. An assay according to claim 4 wherein the test sample is obtained from an animal.

6. An assay according to claim 5 wherein the animal is a mammal.

7. An assay according to claim 6 wherein the mammal is selected from the group comprising cows, sheep, dogs, cats, goats, pigs, horses and humans.

8. An assay according to claim 4 wherein the assay is used to test newborns in order to determine if the newborn has a fatty acid oxidisation disorder.

9. An assay according to claim 8 wherein the fatty acid oxidisation disorder results in alteration of acyl CoA levels.

10. An assay according to claim 9 wherein the fatty acid oxidisation disorder in MCAD deficiency.

11. An assay according to claim 4 wherein the source of the test sample is from the blood or urine.

12. An assay according to claim 4 wherein the derivatizing agent is an agent which upon reaction with a acyl CoA renders the acyl CoA sufficiently fluorescent such that the fluorescent acyl CoA derivative can be detected at low concentrations.

13. An assay according to claim 12 wherein the fluorescent acyl CoA derivative is detected at concentrations of less than 100 pmoles.

14. An assay according to claim 12 wherein the fluorescent acyl CoA derivative is detected at concentrations of less than 5 pmoles.

15. An assay according to claim 12 wherein the fluorescent derivative of acyl CoA is formed using amine reactive probes, amine derivatization reagents or protein labelling reagents.

16. An assay according to claim 15 wherein the reagents modify the amine group on the coenzyme A adenine ring to form fluorescent derivatives.

17. An assay according to claim 16 wherein the reagents are selected from the group comprising chloroacetaldehyde, dansyl or dabsyl chloride, napthalene-2,3-dicarboxyaldehyde (NDA), fluorescein, and o-phthaldialdehyde (OPA).

18. An assay according to claim 4 wherein the fluorescent derivatives of the acyl CoA esters are detected using a fluorometer.

19. An assay according to claim 4 wherein the acyl derivatives in the test sample are separated.

20. An assay according to claim 19 wherein the acyl derivatives are separated using HPLC techniques.

21. An assay according to claim 4 wherein a control sample comprising known amounts of particular acyl CoA esters having varying length acyl groups is run in conjunction with the test sample in order to allow identification and quantification of the acyl CoA esters in the test sample.

22. An assay according to claim 21 wherein the control sample is a normal sample from a healthy organism which does not have a fatty acid oxidation disorder.

23. A kit for use with the assay of claim 4, the kit comprising
   a derivatizing agent for fluorescently derivatizing an acyl CoA ester(s) present in a test sample; and
   a normal and/or control sample for comparing the level of said acyl CoA ester(s) in the test sample with the level of acyl CoA ester(s) in the normal and/or control sample.

24. A kit according to claim 23 wherein the normal and/or control sample(s) is already derivatized.

25. A kit according to claim 23 wherein the normal and/or control sample(s) is derivatized in conjunction with the test sample by the derivatizing agent.

26. A method for measuring levels of acyl coenzyme A (acyl CoA) esters in a sample, comprising the steps of:
   a) forming a reaction mixture comprising the sample to be tested and a derivatizing agent;
   b) allowing the sample and said derivatizing agent to react, so as to form substantially, intact fluorescent derivatives of any acyl CoA esters present in the sample;
   c) separating by size the substantially intact fluorescent derivatives; and
   d) determining levels of said substantially intact fluorescent derivatives.

* * * * *